United States Patent [19]

Bogoch

[11] 4,195,017

[45] Mar. 25, 1980

[54] MALIGNIN, DERIVED FROM BRAIN TUMOR CELLS, COMPLEXES AND POLYPEPTIDES THEREOF

[76] Inventor: Samuel Bogoch, 46 E. 91st St., New York, N.Y. 10028

[21] Appl. No.: 852,198

[22] Filed: Nov. 17, 1977

Related U.S. Application Data

[63] Continuation of Ser. No. 553,075, Feb. 25, 1975, abandoned, which is a continuation-in-part of Ser. No. 550,432, Feb. 18, 1975, Ser. No. 450,404, Mar. 12, 1974, and Ser. No. 385,451, Aug. 3, 1973.

[51] Int. Cl.² .................... A61K 39/00; C07C 103/52; C07G 7/00

[52] U.S. Cl. ........................... 260/112 R; 260/112 B; 260/112.5 R; 424/8; 424/85; 424/88; 424/95; 424/177

[58] Field of Search .................. 424/8, 12, 85, 88, 95, 424/177; 260/112 R, 112 B, 112.5

*Primary Examiner*—Anna P. Fagelson
*Attorney, Agent, or Firm*—Kenyon & Kenyon

[57] ABSTRACT

A product, Malignin, derived from brain tumor cells, which cells may be cultured in a suitable nutrient medium for many generations, and the method of preparing same. Malignin may be complexed with an inert carrier, such as bromoacetylcellulose, and employed in tests for brain tumors. The antibody to Malignin is also prepared. A complex of Malignin and an inert carrier may be further complexed with Anti-Malignin.

11 Claims, No Drawings

MALIGNIN, DERIVED FROM BRAIN TUMOR CELLS, COMPLEXES AND POLYPEPTIDES THEREOF

CROSS REFERENCES TO OTHER APPLICATIONS

This is a continuation of application Ser. No. 553,075 filed Feb. 25, 1975, now abandoned which is a continuation-in-part of each of my applications Ser. No. 550,432, filed Feb. 18, 1975, entitled RECOGNIN AND THEIR CHEMORECIPROCALS, Ser. No. 450,404, filed Mar. 12, 1974 and Ser. No. 385,451, filed Aug. 3, 1973.

THE INVENTION

This invention is directed to a novel group of compounds, herein termed Recognins. Recognins are made by treating tumor cells or artificial cancer cells and separating the desired products. The Recognins may be used to prepare their Chemoreciprocals, i.e., by contacting the Recognins for the Recognins on a support with body fluids. These Chemoreciprocals are useful for diagnostic and therapeutic purposes, i.e., for diagnosing and treating cancers.

One of the Recognins of the present invention is Astrocytin. Astrocytin is produced from brain tumor tissue, preferably brain glioma tumor tissue. Protein fractions containing the Astrocytin precursor are first extracted from the tissue. A preferred method of accomplishing the extraction is to treat the tissue with a neutral buffer under conditions of homogenization or other techniques to disrupt the cells and tissues in order to solubilize protein fractions which contain the Astrocytin precursor.

At this point, the Astrocytin precursor is still bound to many large molecular weight substances including protein, glycoproteins, lipoproteins, nucleic acids, nucleoproteins, etc. The solubilized proteins are then separated from the resultant tissue extract. The extract solution from the tissue is then clarified to remove insoluble particles. The low molecular weight contaminants are then removed from the resultant solution, by a perevaporation concentration technique. The solution which is obtained is then treated to cleave Astrocytin precursor from other contaminants in order to obtain the protein fraction having a pK range between 1 and 4. Thus, for example, the solution is placed on a chromatographic column and eluted with increasingly acidic solvents. All of the fractions which are eluted in the neutral or acid range down to pK 4 are discarded and those fractions with pK range 1-4 are collected. The eluate is then treated to obtain a product having a molecular weight of about 8,000. This is accomplished, for example, by first filtering the material to remove low molecular weight substances, i.e., those below 1,000 molecular weight, and filtering again to remove those above 25,000. The fraction having a molecular weight between 1,000 and 25,000 is then further treated, i.e., by thin layer gel (TLG) chromatography, to obtain Astrocytin.

Thus Astrocytin may be produced by extracting brain glioma tumor tissue with a neutral buffer, by repeated homogenization and high speed centrifugation, separating from the resulting extract the fraction having a pK range of from about 1 to 4, separating from said fraction the substances having a high molecular weight, i.e., up to about 230,000, and isolating therefrom the product Astrocytin having a molecular weight of about 8,000.

The product Astrocytin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mµ and having a molecular weight of about 8,000.

Astrocytin is also characterized by having a very high percentage of residues of glutamic acid and aspartic acid and a very high ratio of these acids to histidine. A further analysis of Astrocytin is provided below.

In a manner similar to that described above, another Recognin, called Malignin, is produced from artificial cancer cells, i.e., cancer cells grown in vitro. Malignin has a molecular weight of about 10,000 and similar but distinct amino acid residue composition to Astrocytin, i.e., high ratios of glutamic acid and aspartic acid and high ratios of these acids to histidine. A further analysis of Malignin is provided below.

Thus, Malignin can be produced by extracting artificial cancer cells grown in culture with a neutral buffer by repeated homogenization and high speed centrifugation, separating from the resulting extract the fraction having a pK range of about 1 to 4, separating from said fraction the substances having a high molecular weight, i.e. up to about 230,000, and isolating therefrom the product having a molecular weight of about 10,000.

Malignin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mµ and having a molecular weight of about 10,000.

Recognins are further characterized by being capable of complexing with bromoacetylcellulose to form bromoacetylcellulose-Recognin and producing the specific antibodies Anti-Recognin upon injection into mammals, said Anti-Recognin being toxic to brain tumor cells in vitro and producing fluorescence of glioma cells when coupled with fluorescein, as described in further detail below.

Recognins, such as Astrocytin, Malignin and similar substances are useful as products which may be introduced into a biological system to reduce foreign reactions, such as by coating a material with a Recognin. A further example may be to introduce a Recognin in order to produce the Chemoreciprocals in the biological system. They may also be used nutritionally to encourage the growth of a particular biological system of which they are a part. A further utility of Recognin is the production of Target reagents which comprise the complexes of the Recognin with a carrier to facilitate its applicability in biological systems. Thus, for example, the complex conveys the physical-chemical characteristics of the Recognin itself. The carrier should be selected from those which form a complex with the Recognin and which are substantially biologically inert.

Any substance known in the art which will form a stable complex with polypeptides or proteins may be useful for complexing with the Recognin. An example is a cellulose-based material, such as bromoacetyl-cellulose. In addition to being inert to the biological system, the carrier should be one that does not alter the specific physical-chemical properties of the Recognin which are useful for the purposes set forth herein.

The complexes of the Recognin and its carrier are useful for producing, separating and identifying its chemoreciprocal in any biological system with which it is brought into contact. The Recognin-carrier complex is also useful for stimulating the production of its chemoreciprocal precursor in any biological system into which it is introduced.

One class of Chemoreciprocals are the anti-Recognins, i.e. anti-Astrocytin and anti-Malignin. These may be made by injecting the Recognin into a biological system. An immunologically effective dose of Recognin is brought into contact with bodily tissues or fluids in a manner which induces an antibody response in accordance with techniques known in the art for producing antibodies. The anti-Recognins may be used for the delivery of materials such as diagnostic, nutritional and therapeutic agents to specific cells or sites in a biological system which comprises introducing said agent in complexed form with the anti-Recognin into the biological system. The anti-Recognins are also useful for diagnosing the presence of tumor cells in a histology section, by applying the Anti-Recognin conjugated with a labeling substance such as dyes and radioactive substances, to said section, whereby staining or radioactive labeling occurs only with tumor cells. Yet another use for anti-Recognins is for increasing the yield of other useful Chemoreciprocal products (such as TAG, described below) from a mammal which comprises injecting an immunologically effective dose of Recognin into the mammal, or other biological system.

Another class of Chemoreciprocals is Target reagents complexed with their chemoreciprocals. For example, the Target product of Astrocytin complexed with a carrier such as bromoacetylcellulose is brought into contact with anti-Astrocytin. This type of compound may be complexed with and used for the delivery of diagnostic, nutritional and therapeutic agents to specific cells or sites in a biological system. These compounds may also be used for purification procedures. For example, Anti-Astrocytin may be made by the decomplexing of Bromoacetylcellulose-Astrocytin-Anti-Astrocytin by hydrolytic treatment with an acid or proteinase enzyme. Target reagents are also useful for increasing the amount of TAG products (described below) in a biological system, such as by bringing an immunologically effective dose of Target into contact with bodily tissues or fluids.

Additional Chemoreciprocals are TAG reagents (e.g. Target-Attaching Globulins). The TAG products are produced by bringing Target reagents into contact with body fluids for varying periods of time to form a complex and cleaving TAG therefrom. Two useful embodiments are S-TAG and F-TAG.

A process for producing S-TAG (Slow-Target-Attaching-Globulin) comprises reacting blood serum or other body fluid with Target (i.e. Bromoacetylcellulose-Malignin) for approximately two hours or more at a low temperature, e.g. about 4° C., and cleaving S-TAG from the resulting material, e.g. with dilute acid for approximately two hours at a temperature of about 37° C. The product S-TAG prepared in accordance with this process is characterized by being soluble in aqueous buffered solutions, forming a single line precipitate with its corresponding Recognin in Ouchterlony gel diffusion tests, being non-dialyzable in cellophane membranes, being retained by millipore filters which retain molecules over 25,000 molecular weight, having molecular weights in different states of aggregation as determined by thin layer gel chromatography of approximately 50,000, and multiplies thereof into the macroglobulin range and having a spectrophotometer absorption peak wave length of 280 m$\mu$.

A process for producing F-TAG (Fast-Target-Attaching-Globulin) comprises reacting blood serum or other body fluid with Target (i.e. Bromoacetylcellulose-Malignin) for approximately 10 minutes at a low temperature, e.g. about 4° C., and cleaving F-TAG from the resulting material, e.g. with dilute acid for approximately two hours at a temperature of about 37° C. The product F-TAG prepared in accordance with this process is characterized by being soluble an aqueous buffered solutions, forming a single line precipitate with its corresponding Recognin in Ouchterlony gel diffusion tests, being non-dialyzable in cellophane membranes, being retained by millipore filters which retain molecules over 25,000 molecular weight, having molecular weights in different states of aggregation as determined by thin layer gel chromatography of approximately 50,000, and multiples thereof into the macroglobulin range and having a spectrophotometer absorption peak wave length of 280 m$\mu$.

TAG products are useful for detecting cancer tumors in living mammals by determining the concentration of S-TAG and F-TAG produced by a known volume of the mammal's blood serum or other body fluid and correlating this concentration with amounts determined to be indicative of cancer. TAG products are also useful for diagnosing the presence of tumor cells in a histology section, which comprises applying TAG conjugated with a labeling substance such as dyes and radioactive substances, to said section, whereby staining or radioactive labeling occurs only with tumor cells. TAG products additionally have been found to be cytotoxic to tumor cells. TAG products are also useful for directing the delivery of diagnostic, nutritional and therapeutic agents to specific cells or sites by introducing said agents in complexed form with the TAG product.

Normal cell division in plants or animals is restricted or inhibited when the cells come to occupy fully a particular space. The mechanisms (a) by which normal cells "recognize" that they have filled the space available to them, and (b) by which the operation of this recognition mechanism in turn inhibits cell division, have both been unknown. The inventor has produced a group of compounds whose precursors are increased in concentration when normal recognition and learning occur, and which relate to recognition and learning in particles and cells, and with the connection of cells to each other. These compounds are termed RECOGNINS by the inventor. By attempting to produce these compounds from normal cancer cells, the inventor has discovered that they are absent as such, and that changes in their molecular structure have occurred at the same time that the cancer cells have lost their ability (a) to recognize that they have filled their normal volume, and/or (b) to stop dividing when they have filled their normal volume.

The inventor has discovered novel compounds and methods for producing such compounds. These new compounds are termed RECOGNINS by the inventor. RECOGNINS are novel compounds which have physicochemical characteristics which mimic those configurations characteristic of cancer cells in terms of their failure to recognize and stop cell division. The use of RECOGNINS goes beyond insight into the cancer mechanism, for immediate products and methods are thereby provided which are useful in the diagnosis and treatment of cancer, and for its prevention.

I have discovered methods by which artificially cultured cells can be used to produce MALIGNINS for the first time. One advantage of the methods disclosed herein is that MALIGNINS and new products from them can now be manufactured efficiently in virtually limitless quantities.

This invention transcends the field of cancer research and is immediately applicable to any and all biological systems in which it is desired to influence all growth and metabolism. Thus by the manufacture of the particular compound or compounds of appropriate cell type in artificial culture, and the further manufacture of products from these substances, specific influence may for the first time be brought to bear on any tissue, cell, cell organelle, sub-organelle molecule or molecular aggregate in any living system. Thus specific nutritional influences at critical times in development, specific diagnostic, preventative and treatment methods, and the construction of artificial bioelectrical systems (as in tissue or organ transplants) can all be affected for the first time. These artificial bioelectrical systems can now be made to bear the characteristics of the specific RECOGNIN, MALIGNIN or their CHEMORECIPROCALS of the normal tissue or component which they will neighbor and thus avoid being "recognized" as "foreign" and thus avoid the reactions to alien substances, including rejection.

Another aspect of this invention is the production of a valuable specific antibody-like product (Anti-Astrocytin) to a specific brain product (Astrocytin), permitting the use of this antibody-like product to specifically complex with and, as a specific delivery vehicle to, specific points in the nervous system of all species. MALIGNINS and ASTROCYTIN and RECOGNINS.

Still another aspect of this invention is the production from biological fluids of two new products, TARGET-ATTACHING-GLOBULINS (TAG), which are so named because they are produced by two reactions, the first reacting biological fluids with a synthetic complex containing physicochemical configurations which mimic those of the MALIGNINS and called TARGET, the second, cleaving the specific TAG from the complex, and by the measure of the TAG so produced obtaining a quantitative indication from the biological fluids of living organisms whether there is present a tumor in that organism; hence a diagnostic test for tumors. Because TAG products and ANTI-MALIGNIN are physicochemically complimentary to MALIGNINS, they are termed CHEMORECIPROCALS.

I have further discovered that two quantitatively and qualitatively distinct TAG products can be produced depending upon the time permitted for the reaction of serum with the specific TARGET reagent used, and depending upon the time permitted for the cleavage of the product which has been complexed.

After examining the amounts of these products which could be produced from a number of different individuals with brain tumors and various other medical disorders, as well as in those with no apparent disease process, it became apparent that the amounts of these two new products which could be produced in a given individual was indicative of whether that individual had a brain tumor, hence a serum diagnostic test for brain tumors, the first to my knowledge.

The utility of these new products, in addition to their use to diagnose from serum and other biological fluids the presence of brain and other tumors, is illustrated by the demonstration that TAG and anti-RECOGNIN compounds attach to glial tumor cells preferentially in histological sections of brain tumor and surrounding tissue removed at surgery of the brain tumor. This preferential labelling by TAG and Anti-RECOGNINS of tumor cells is demonstrated through standard immunofluorescent techniques. Thus a new method is also available for determining through histological examination with a new degree of certainty whether tumor cells are present in the tissue removed, and whether these tumor cells have penetrated to the very edges of the tissue removed indicating the likelihood that tumor still remains in the brain or other organ, or that tumor cells are absent from the periphery of the tissue removed, indicating the possibility that all of the tumor has been removed from the brain or other organ. In addition, TAG and Anti-RECOGNINS produced as described have been found to be cytotoxic for glioma brain tumor cells grown in tissue culture in vitro. This high affinity for tumor cells in another medium, here grown in tissue culture, is further evidence of the specific-coupling potential of the new product TAG, and explains the adoption of the name TARGET-ATTACHING-GLOBULINS (TAG) as do TAG's properties in regard to the synthetic product TARGET, and to tumor cells in histological section. Further, the cytotoxicity of TAG and anti-RECOGNINS for tumor cells provides an additional new diagnostic test for serum of patients who are suspected of suffering from a tumor. Thus, for example, the serum or other body fluid of these patients is reacted with TARGET to produce TAG and the product TAG is tested in tissue culture growths of tumor cells for cytotoxicity. Both the concentration of TAG and the degree of cytotoxicity manifested by the TAG which can be produced from a given individual's serum may be not only diagnostic but also of value in tracing the course of the disorder preoperatively and postoperatively in a given patient. Coupling of radioactive and dye tracers to TAG provides new TAG products which are useful in vivo in the diagnosis of tumors and in their exact localization. Thus the injection of suitably labelled TAG either intraarterially or intravenously, into the cerebrospinal fluid, or directly into brain tissue or its cavities, permits the demonstration by radioactive means, or by visualization of the coupled dye, of the presence of a brain tumor, for it is only to the tumor cells that the TAG specifically attaches. Further, this method permits the precise visualization of the location of the brain tumor. This can be seen to be an improvement of this in vivo diagnostic method using anti-ASTROCYTIN produced in rabbit blood to label the brain tumor, because the use of TAG produced from human serum avoids the possibility of foreign protein reactions. Since TAG and anti-RECOGNINS have the chemical specificity which permits preferential attachment to ASTROCYTIN precursor containing tumor cells both in vitro and in vivo, these products may also be used therapeutically, as well as diagnostically, when coupled, e.g., with radioactive, proton capture agents, or other toxic physical or chemical agents, so that these toxic substances may be localized preferentially through these compounds' specificity of attachment in the tumor cells as compared to their neighboring normal cells. This selectivity is universally recognized as the crucial, or at least one crucial factor for achieving effective chemical or physical therapy of tumors, and a factor which has hitherto not been achieved. Thus TAG has demonstrated efficacy in attaching preferentially to the tumor cells, and should have promise as a new therapeutic product for these reasons.

In the serum of patients with malignant tumors, as will be seen in the examples below, one type of TAG, SLOW-TAG (S-TAG) as distinguished from FAST-TAG (F-TAG), can be produced in relatively greater amounts from a given volume of serum than in patients without such tumors. This suggests that either one of TAG's naturally occuring precursors (P-TAG) is increased in concentration or that other factors exist which favor the relative in vitro production of S-TAG over F-TAG.

The possible relationship of the function of the actual synthetic products TARGET and TAG to their precursors, and in turn to functions of postulated but not demonstrated cell "antigens" and circulating "antibodies" to them which may exist in vivo has yet to be elucidated. Thus for example, in antibody-like fashion, F-TAG and S-TAG produce single discrete lines of reaction with ASTROCYTIN in Ouchterlony gel diffusion, and the injection of TARGET in rabbits induces an increase in the yield of TAG products from rabbit serum after reacting with TARGET. The finding that there may be a normal level of a precursor resembling circulating antibody to a cell antigen which is hidden in the non-dividing cell raises a question as to the possible function of the pair. It is here proposed that TAG precursor (P-TAG) and TARGET-like substances exist in vivo which function in the control of cell proliferation and cell death. Thus, for example, the exposure of a cell constituent which normally is not directly exposed to serum proteins may occur during cell division. The exposure of this cell constituent could result in that constituent becoming converted to a TARGET-like substance to which the attachment of a P-TAG-like molecules from serum may then occur, which would stimulate cell division or inhibit it. Alternatively, a non-dividing cell which is injured or malfunctioning may expose a TARGET-like substance to which the attachment of P-TAG-like molecules may be reparative. However, under certain cell conditions the attachment of P-TAG-like molecules may induce the destruction of the cell (e.g. ANTI-GLIOMA-TAG synthetically produced as here described is markedly cytotoxic to glioma tumor cells growing in tissue culture). This could thus represent a mirror of a normal mechanism for the control of cell division, and for either the repair or the removal of individual cells in the body throughout the life of the organism. If the exposure of cell constituents is abnormally increased so that abnormally large amounts of cell TARGET-like substances are formed, as may occur in rapidly dividing cancer cells such as in brain gliomas, an increase in the concentration of one type of serum P-TAG relative to another may be induced.

Whatever the actual function of the precursors, the increase in the relative amount of predominantly one type of TAG, SLOW-TAG (S-TAG) which can be produced in vitro by the methods here described from the serum of patients with malignant tumors is the basis of the serum diagnostic test described in the examples which follow.

The following examples illustrate the invention.

EXAMPLE I

Production of Crude ASTROCYTIN-Precursor-Containing Fraction.

Human brain glioma tumor tissue, removed at surgery, is dissected free as possible of surface blood vessels and normal brain tissue. For a typical amount of dissected tumor tissue of 11 grams, the tissue is weighed into six 1.5 g. and two 1.0 g. aliquots. Each aliquot is then treated as follows.

Each aliquot is homogenized in neutral buffer solution by sonification or other mechanical means. For example, each aliquot is homogenized in 100 cc per g. of tissue of 0.005 M phosphate buffer solution, pH 7, in a Waring blender. Homogenization should be done in the cold to prevent denaturation of proteins. For example, the blender should be precooled in a cold room at 0°–5° C. and operated for about only three minutes.

The homogenate is then centrifuged for clarification, for example at 80,000 times gravity for 30 minutes in a refrigerated ultracentrifuge. The soluble supernatant is decanted and kept in the cold. The insoluble residue is rehomogenized with a further 100 cc of neutral buffer and centrifuged as before, and the second soluble extract combined with the first. Best yields are obtained when this procedure of homogenization and centrifugation is repeated until less than 50 micrograms of protein per ml. of solution are obtained in the supernate. With most tissues this is accomplished by the fifth extraction.

The solutions thus obtained are combined and concentrated by perevaporation with subsequent dialysis, as by dialysis against 0.005 M phosphate buffer in the cold to produce a volume of 15 ml. The volume of this solution is noted, an aliquot is taken for total protein analysis, and the remainder is fractionated to obtain the protein fraction having a pK range between 1 and 4. The preferred method of fractionation is chromatography as follows.

The solution is fractionated in the cold room (4° C.) on a DEAE cellulose (Cellex-D) column 2.5×11.0 cm., which has been equilibrated with 0.005 M sodium phosphate buffer. Stepwise eluting solvent changes are made with the following solvents (solutions): Solution (1) 4.04 g. $NaH_2PO_4$ and 6.50 g. $Na_2HPO_4$ are dissolved in 15 liters of distilled $H_2O$ (0.005 molar, pH 7); Solution (2) 8.57 g. $NaH_2PO_4$ is dissolved in 2480 ml. of distilled $H_2O$; Solution (3) 17.1 g. of $NaH_2PO_4$ is dissolved in 2480 ml. of distilled $H_2O$, (0.05 molar, pH 4.7); Solution (4) 59.65 g. of $NaH_2PO_4$ is dissolved in 2470 ml. distilled $H_2O$ (0.175 molar); Solution (5) 101.6 g. of $NaH_2PO_4$ is dissolved in 2455 g. distilled $H_2O$ (0.3 molar, pH 4.3); Solution (6) 340.2 g. of $NaH_2PO_4$ is dissolved in 2465 ml. of distilled $H_2O$ (1.0 molar, pH 4.1); Solution (7) 283.64 g. of 80% phosphoric acid ($H_3PO_4$) is made up in 2460 ml. of distilled $H_2O$ (1.0 molar, pH 1.0).

Add nervous tissue extract, 6 to 10 ml. volume. Let it pass into column. Then overlay with Solution (1) and attach a reservoir of 300 ml. of Solution (1) to drip by gravity onto the column. Three ml. aliquots of effluant are collected by means of an automatic fraction collector. The subsequent eluting solutions are exchanged stepwise at the following elution tube numbers. Solution (2): at tube 88, bring solution on column to top of resin, then overlay and attach reservoir of 50 ml. of Solution (2); Solution (2); at tube 98, bring solution on column to top of resin, then overlay and attach reservoir of 75 ml. of Solution (3); Solution (4): at tube 114, bring solution on column to top of resin, then overlay and attach reservoir of 150 ml. of Solution (4); Solution (5): at tube 155, bring solution on column to top of resin, then overlay and attach reservoir of 125 ml. of Solution (5); Solution (6): at tube 187, bring solution on column to top of resin, then overlay and attach reservoir of 175 ml. of Solution (7); continue eluting until at tube 260, elution is complete. Use freshly prepared resin for every new volume of tissue extract. Each effluent tube is quantitatively analyzed for protein. The elutes in the tube numbers 212 to 230 are combined, and contain the crude products from which ASTROCYTIN will be produced.

While data has been published on this crude material, called fraction 10B in the past, [Protein Metabolism of the Nervous System,] pp. 555–69 (Pleum Press, 1970); Journal of Neurosurgery, Vol. 33, pp. 281–286 (September, 1970)] the cleavage from fraction 10B of the specific product herein called ASTROCYTIN has now been accomplished. Crude fraction 10B can be prepared as a product in amounts between 0.1 and 10 mg. per gm. of original fresh nervous system tissue from which it was obtained. In addition to an ASTROCYTIN-precursor it contains varying amounts of covalently bound carbohydrate residues including a number of hexoses, namely glucose, galatose, mannose; hexosamines, including glucosamine, galatosamine and mannosamine; and occasionally other sugars, such as fucose, ribose and perhaps rhamnose. It also contains large molecular weight protein products, several lipids and nucleic acids.

EXAMPLE 2

Production of Purified ASTROCYTIN from Crude ASTROCYTIN-Precursor-Containing Fraction.

The ASTROCYTIN-Precursor-Containing fraction is further isolated from contaminants. In the preferred embodiments, the material from Example 1 is chromatographed on Sephadex G-50 resin with a typical column of 40 cm. long, 2.5 cm. diameter, and 196 ml. volume. The pressure used is 40 mm. Hg.; the flow rate is 35 ml. per hour, and the buffer is 0.05 molar phosphate buffer solution, pH 7.2. The first (flow-through) peak contains ASTROCYTIN-Precursor together with impurities, whereas subsequent peaks contain only impurities.

In the preferred embodiment, the products in the above first flow-through peak are then concentrated on Sephadex G-15, then passed onto a column of Cellex-D with the same solutions, (1) through (7) as Example 1, and the same elution steps as performed in Example 1. The product ASTROCYTIN is present as a sharp peak in the same tubes (numbers 212–230) as before, thus maintaining its behaviour on Cellex-D chromatography without the presence of a large number of contaminants.

Low molecular weight contaminants may then be removed by techniques known to the art, such as millipore disc filtration. In the preferred method, the product ASTROCYTIN is freed of salt and other small molecular weight contaminants by filtration through Millipore Pellicon Disc No. 1000, 13 mm., which retains substances of molecular weight greater than 1000 and permits to pass through those of molecular weight less than 1000. The product ASTROCYTIN remains on the Pellicon Disc, and is recovered from it by washing with Solution (1) of Example 1.

ASTROCYTIN is then obtained by isolating the compound having a molecular weight of about 8000 from the above solution. A preferred method uses thin layer gel (TLG) chromatograph as follows:

The apparatus used is the commercially available one designed by Bochringer Mannheim GmbH; Pharmacia Fine Chemicals and CAMAG (Switzerland). The resin 2.5 g. of Sephadex G-200 superfine is prepared in 85 ml. of 0.5 M NaCl in 0.02 M. $Na_2HPO_4KH_2PO_4$ Phosphate Buffer ph 6.8 (6.6–7.0). Allow to swell two or three days at room temperature with occasional gentle mixing. (Magnetic and other stirrers should not be used). The swollen gel is stabilized for three weeks at refrigerator temperature; however, bacterial and fungal growth may interfere with the swollen gel. If the gel is to be kept for longer periods of time, a small amount of a bacteriostatic agent should be added (sodium Azide 0.02%) 2.5 g. of dry gel are used to make two 20×20 cm. glass plates of 0.5 mm. thick. The plates are either allowed to dry at room temperature for 10 minutes and transferred to a moist chamber where they can be stored for about two weeks, or they are used immediately after appropriate pre-equilibration. (Usually during the night for a minimum of 12 hours). The main function of equilibration is to normalize the ratio between the stationary and mobile phase volumes. With the pre-equilibrated plates in a horizontal position, substances to be determined are applied with micropipettes as spots or as a streak at the start line. 10 ml. to 20 ml. of 0.2–2% protein solution is placed on the edge of a microscopic cover slide (18×18 mm.) and held against the gel surface. In a few seconds the solution will soak into the gel. All samples are first prepared on the cover slides and then quickly applied. If not enough material is used, it is difficult to locate individual spots after separation. If too much material is applied no defined separation occurs. The samples are diluted with buffer for easier handling and the separation of samples is carried in a descending technique with the plate at an angle of 22°. The flow rate of about 1–2 cm/hour is most suitable. Marker substances (such as cytochrome C, haemoglobin, myoglobin or bromophenol Blue labeled albumin) are applied at different positions across the plate to give a check on possible variation of flow across the plate and also to serve as reference proteins for calculation of relative distance (mobility) of unknowns. After application of samples, the plates are replaced in the apparatus and the paper wick pushed slightly downwards to ensure good contact with the gel layer. The paper wick must not drip. Excess moisture is wiped off. The liquid solvent in the reservoir is kept constant at 1 cm. from the upper end of the vessel. The runs are usually completed in 4 to 7 hours depending on the progress of separation. With colored substances separation follows directly. The separated spots of protein are easily made visible by transferring them to a paper sheet replica of TLG plate after the chromatographic separation has been completed, and by staining them on the prewashed methanol+$H_2O$+acetic acid-90:5:5, for 48 hours. The paper sheet is 3 mm. filter paper. A sheet of paper 20×18 cm. is placed over the gel layer and pressed (rolled) just enough to ensure contact with the gel. Care is taken not to trap air under the paper (replica) and not to disturb the gel layer. The liquid phase is soaked off from the gel layer by the paper and removed after about one minute, immediately dried in an oven at a 60° temperature for 15 minutes and stained in the normal way with any of the routine staining procedures. Staining is performed by spraying the replica-paper with 0.03% diazotized sulfanilic acid in 10% Sodium Carbonate (Pauley's Reagent). Staining can also be accomplished with a saturated solution of Amido Black in Methanol-Acetic Acid (90:10 v/v is used); the staining time is 5-10 minutes. For destaining, rinse with two volumes of the 90:10 methanol and acetic acid solution mixed with one volume of H₂O. It is difficult to obtain low background staining without very extensive washing. The plates themselves may also be dried at about 60° C. (in an oven with air circulation) but only if the ASTROCYTIN is to be stained. For isolation purposes, the plate should only be air dried at room temperature. Over-heating can lead to cracking, but this can usually be avoided with at 50°-60° C. temperature which dries a Sephadex G-200 plate in 15-30 minutes. The dry plates are allowed to swell for 10 minutes in a mixture of methanol+H₂O+acetic acid (75:20:5) and stained in a saturated Amido Black in the same solvent system for five hours and subsequently washed by bathing for two hours in the same solvent before they are dried. For molecular weight determinations the distance from the starting line to the middle of each zone is measured with an accuracy of 0.05 mm. either directly on the print (replica) or on the densitogram. The result is expressed by the $R_m$ value defined as the ratio of the migration distance of the tested protein ($d_p$) to that of cytochrome C or myoglobin ($d_m$) which is used as the reference protein: Relating migration distance of tested substance to standard is the formula ($-R_m = (d_p/d_m)$). A straight calibration line is obtained by plotting the logarithm of the molecular weight of the standards used against the $R_m$. From this line the molecular weight of the unknown protein can be obtained. For most exact results six equal parts of the protein sample solution with standard, in this case, cytochrome C, before applying to the plate. By the above TLG procedure the product ASTROCYTIN is observed as a discrete spot at a distance of approximately 0.83±0.02 with reference to the standard cytochrome C, yielding an approximate molecular weight of 8000 for ASTROCYTIN. Several discrete products are separated in this procedure from ASTROCYTIN on the basis of slight differences in chemical structure and large differences in molecular weight. Thus, three products carried as contaminants to this point with molecular weight of approximately 64,000, 148,000 and 230,000, and one occasionally of molecular weight 32,000, have been detected and removed by the TLG methods described above. The product is ASTROCYTIN is aspirated with the gel in which it is contained, in dry form, dissolved in Solution (1) and freed of resin by centrifugation or other similar means.

The product ASTROCYTIN which has been produced at this stage is soluble in distilled water, soluble at neutral and acid pH, and insoluble at alkaline pH and has a spectrophotometric absorption peak wavelength of 280 mμ. It is a polypeptide with molecular weight, as stated above, of approximately 8000. Its covalently linked amino acids are shown by hydrolysis with 6 N HCl then quantitative automatic determination to have the following average composition of amino acids:

|  | Approximate Number of residues |
|---|---|
| Aspartic acid | 9 |
| Threonine | 5 |
| Serine | 6 |
| Glutamic acid | 13 |
| Proline | 4 |
| Glycine | 6 |
| Alanine | 9 |
| Valine | 4 |
| ½ Cystine | 2 |
| Methionine | 1 |
| Isoleucine | 2 |
| Leucine | 8 |
| Tyrosine | 2 |
| Phenylalanine | 3 |
| Lysine | 8 |
| Histidine | 2 |
| Arginine | 4 |
| Approximate Total | 88 |

Cysteic acid, hydroxyproline, norleucine, ammonia, isodesmosine, desmosine, hydroxylysine, lysinonorleucine, and gamma-aminobutyric acid are all absent in detectable amounts, but a trace of glucosamine may be present.

From 11 grams of the starting brain tumor tissue in EXAMPLE 1, approximately 3 mg. of purified ASTROCYTIN is produced by the above methods.

EXAMPLE 3

Production of MALIGNIN-Precursor in Artificial Cancer Cell Culture.

Generally, sterile technique is scrupulously maintained.

All solutions (e.g. Hank's Balanced Salt (BSS), F-10 Nutrient medium, fetal calf serum, trypsin solution) are incubated at about 35° C. in a water bath for approximately 20 minutes or more before use.

Cells are removed from tumor tissue and grown in vitro for many generations using a suitable medium, such as described below. Pre-rinse beakers to be used with a sterilizing solution, for example 12-proponal plus Amphyl or creoline solution.

In the preferred embodiment, the artificial cancer cells (i.e., cells grown in vitro for many generations) are grown in 250 ml. flasks. The liquid medium in which the cells are growing is discharged into the pre-rinsed beakers. The cells are then washed gently with 5-10 ml. of Hank's BSS or other similar solution for about 30 seconds. Avoid agitation. All walls and surfaces are washed. The solution is clarified of cells by centrifugation in the cold from 10 minutes at 3,000 rpm. The medium is poured into a beaker as above. Add a small amount of buffered proteinase ensyme solution and rinse quickly to avoid digestion of the cells. In the preferred method, 1-2 ml. of trypsin solution (EDTA) is added and rinsed for only 10 seconds. Pour off the trypsin solution.

Add a similar volume of fresh trypsin solution and incubate until the cells are seen to be separated from the walls of the chamber through microscopic observation. This usually requires 5-10 minues. Add a suitable growth medium, such as 50 ml. of a solution of 7-10 percent solution of fetal calf serum in 100 ml. of F-10 Nutrient medium.

Twentyfive ml. of the fresh medium with cells is transferred to a new growth chamber for propagation and the remaining 25 ml. is kept in the first chamber for propagation. Both chambers are placed in an incubator at 35° C. for approximately seven days. By the procedure of this Example to this point, an artificial cancer cell culture is divided into two fresh cultures approximately every seven days. This entire procedure may be repeated as often as desired, at approximately seven-day intervals, for each growth chamber. Thus, the number of cells growing in vitro may be doubled approximately every seven days.

The cells may be extracted for the production of MALIGNIN after approximately seven days of growth. For example, cells growing in each 250 ml. growth chamber as described above, may be recovered as follows.

The medium is transferred to a centrifuge tube and centrifuged at 3,000 rpm in the cold for 10 minutes. The medium is discarded. The cells remaining in the growth chamber are scraped from the chamber walls and washed into the centrifuge tubes with neutral buffer solution. The cells are washed twice with neutral buffer solution, centrifuged again at 3,000 rpm in the cold, and the medium is discarded. The washed cells are suspended in 10 ml. of neutral phosphate buffer until ready for extraction of crude MALIGNIN-Precursor-Containing fraction.

EXAMPLE 4

Production of Crude MALIGNIN-Precursor-Containing Fraction.

Washed cells suspended in neutral buffer from EXAMPLE 3 are mechanically disrupted under conditions which avoid denaturation of most proteins. In the preferred method, the washed cells are treated in the cold with a sonifier for 20 seconds.

After sonification the cell residues are centrifuged at 30,000 rpm for 30 minutes and the supernatant decanted. Ten ml. aliquots of buffer solution are used to wash remaining cells from the chamber and these are added to the remaining cell residues. Sonify and centrifuge as above and combine the supernatants. Repeat the process once more.

The combined supernatant is perevaporated to reduce the approximate 30 ml. volume to about 6–7 ml. An aliquot is taken for total protein analysis and the remainder is fractionated according to the methods of EXAMPLE 1 for ASTROCYTIN Precursor.

EXAMPLE 5

Production of Purified MALIGNIN Product from Crude MALIGNIN-containing Fraction.

The product MALIGNIN is further isolated from contaminants by the methods of EXAMPLE 2 for ASTROCYTIN.

In the TLG step of the preferred embodiment, the product MALIGNIN is observed as a discrete spot at a distance of approximately 0.91±0.02 with reference to the standard cytochrome C, yielding an approximate molecular weight of 10,000 for MALIGNIN.

The product MALIGNIN which has been produced at this stage is soluble in distilled water, soluble at neutral or acid pH, and insoluble at alkaline pH and having a spectrophotometric absorption peak of 280 mu. It is a polypeptide with molecular weight of approximately 10,000. Its covalently linked amino acids are shown by hydrolysis with 6 N HCl then quantitative determination to have the following average composition of amino acids:

|  | Approximate Number of Residues |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cystine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approximate Total | 89 | the amino acids cysteic acid, hydroxyproline, norleucine, ammonia, isodesmosine, desmosine, hydroxylysine, lysinonorleucine and gamma-aminobutyric acid being absent in detectable amounts.

A typical yield of pure MALIGNIN from twelve 250 ml. reaction chambers of EXAMPLE 3 together is approximately 1 mg. of MALIGNIN.

EXAMPLE 6

Production of TARGET Reagents from RECOGNINS.

ASTROCYTIN, prepared as in EXAMPLE 2 above, or MALIGNIN, prepared as in EXAMPLE 5 above, is complexed with a carrier to produce TARGET reagent.

In the preferred embodiment, ASTROCYTIN or MALIGNIN is dissolved in 0.15 M $NaH_2PO_4$—citrate buffer, pH 4.0. A bromoacetyl-resin, for example bromoacetylcellulose (BAC) having 1.0 to 1.5 milliequivalents Br per gram of cellulose, stored in the cold, is prepared in 0.15 M $NaH_2PO_4$ buffer, pH 7.2. Convert the buffer to pH4 by pouring off the pH 7.2 buffer solution and adding 0.15 M $NaH_2PO_4$—citrate buffer, pH 4.0. The ASTROCYTIN or MALIGNIN solution and the BAC solution are stirred together (10:1 BAC to RECOGNIN ratio) for 30 hours at room temperature, then centrifuged.

It is preferred that all sites on the BAC which are available to bind to RECOGNIN be bound. This may be accomplished as follows. The supernatant from the immediately preceding step is lyophilized and the protein content determined to indicate the amount of ASTROCYTIN or MALIGNIN not yet complexed to BAC. The complexed BAC-ASTROCYTIN (or BAC-MALIGNIN) is resuspended in 0.1 M bicarbonate buffer pH 8.9, stirred 24 hours at 4° to permit the formation of chemical bonds between the BAC and the ASTROCYTIN or MALIGNIN. After the 24 hours, the suspension is centrifuged and supernatant analyzed for protein. The complexed BAC-ASTROCYTIN or BAC-MALIGNIN is now resuspended in 0.05 M aminoethanol—0.1 M bicarbonate buffer pH 8.9 in order to block any unreacted bromine. The suspension is centrifuged, and the supernatant is kept but not analysed because of the presence of aminoethanol. Removal of all unbound ASTROCYTIN or MALIGNIN is then accomplished by centrifugation and resuspension for three washings in 0.15 M NaCl until no absorbance is measured on the spectrophotometer at 266 mµ. The BAC-ASTROCYTIN or BAC-MALIGNIN complex is now stirred in 8 M urea for 2 hours at 38° C., centrifuged, then washed (three times usually suffices) with 8 M urea until no absorbance is shown in the washings at 266 mµ. The complex is then washed with 0.15 M NaCl two times to rid of urea. The complex is then stirred at 37° C. in 0.25 M. acetic acid for 2 hours to demonstrate its stability. Centrifuge and read supernatant at 266 mµ—no absorbance should be present. This chemically complexed BAC-ASTROCYTIN or BAC-MALIGNIN is therefore stable and can now be used as a reagent in the methods described below; in this stable reagent form it is referred to as TARGET (TOPOGRAPHIC-ANTIGEN-LIKE-REAGENT-TEMPLATE) because it is a synthetically produced complex whose physical and chemical properties mimic the stable cell-bound precursor of ASTROCYTIN or MALIGNIN when it is in a potential reactive state with serum components. For storing, TARGET reagent is centrifuged and washed until neutralised with 0.15 M NaH$_2$PO$_4$ buffer pH 7.2.

TARGET reagents may be prepared from bromoacetyl liganded carriers other than cellulose, such as bromoacetylated resins or even filter paper.

EXAMPLE 7

Production of antisera to Astrocytin, Malignin and TARGET.

Antisera to Astrocytin, Malignin or TARGET reagents may be produced by inducing an antibody responce in a mammal to them. The following procedure has been found to be satisfactory.

One mg. of RECOGNIN (Astrocytin or Malignin) is injected into the toe pads of white male rabbits with standard Freund's adjuvant, and then the same injection is made intraperitoneally one weak later, again intraperitoneally ten days and, if necessary, three weeks later. Specific anitbodies may be detected in the blood serum of these rabbits as early as one week to ten days after the first injection. The same procedure is followed for TARGET antigen by injecting that amount of TARGET which contains 1 mg. of Astrocytin or Malignin as determined by Folin-Lowry determination of protein.

The specific antibody to Astrocytin is named Anti-Astrocytin. The specific antibody to Malignin is named Anti-Malignin. Similarly, the specific antibody to TARGET reagent is named Anti-Target.

These antibodies show clearly on standard Ouchterlony gel diffusion tests for antigen-antibody reactions with specific single sharp reaction lines produced with their specific antigen.

The presence of specific antibodies in serum can also be tested by the standard quantitative precipitin test for antigen-antibody reactions. Good quantitative precipitin curves are obtained and the micrograms of specific antibody can be calculated therefrom.

Further evidence of the presence of specific antibodies in serum can be obtained by absorption of the specific antibody Anti-Astrocytin onto Bromoacetyl-cellulose-Astrocytin (BAC-Astrocytin) prepared above. The antiserum containing specific Anti-Astrocytin can be reacted with BAC-Astrocytin. When the serum is passed over BAC-Astrocytin only the specific antibodies to Astrocytin bind to their specific antigen Astrocytin. Since Astrocytin is covalently bound to Bromoacetyl-cellulose the specific antibody, Anti-Astrocytin, is now bound to BAC-Astrocytin to produce BAC-Astrocytin-Anti-Astrocytin (BACA-Anti-Astrocytin). This is proved by testing the remainder of the serum which is washed free from BAC-Astrocytin. On standard Ouchterlony diffusion no antibodies now remain in the serum which will react with Astrocytin. It is therefore concluded that all specific antibodies (Anti-Astrocytin) previously shown to be present in the serum, have been absorbed to BAC-Astrocytin. Furthermore, when Anti-Astrocytin is released from its binding to BAC-Astrocytin it is thereby isolated free of all contaminating antibodies. This release of Anti-Astrocytin may be accomplished by washing the BACA-Anti-Astrocytin compled with) 0.25 M acetic acid (4° C., 2 hrs.) which has been shown above not to break the BAC-Astrocytin bond.

Still further evidence of the presence of specific antibodies in serum can be obtained by adsorption of the specific antibody Anti-Malignin onto Bromoacetyl-cellulose-Malignin (BAC-Malignin) prepared above. The antiserum containing specific Anti-Malignin can be reacted with BAC-Malignin. When the serum is passed over BAC-Malignin only the specific antibodies to Malignin bind to their specific antigen Malignin. Since Malignin is covalently bound to Bromoacetyl-cellulose the specific antibody, Anti-Malignin, is now bound to BAC-Malignin to produce BAC-Malignin-Anti-Malignin (BACM-Anti-Malignin). This is proved by testing the remainder of the serum which is washed free from BAC-Malignin. On standard Ouchterlony diffusion no antibodies now remain in the serum which will react with Malignin. It is therefore concluded that all specific antibodies (Anti-Malignin) previously shown to be present in the serum, have been absorbed to BAC-Malignin. Furthermore, when Anti-Malignin is released from its binding to BAC-Malignin it is thereby isolated free of all contaminating antibodies. This release of Anti-Malignin may be accomplished by washing the BACM-Anti-Malignin complex with 0.25 M acetic acid (4° C., 2 hrs.) which has been shown above not to break the BAC-Malignin bond.

The antibodies to TARGET show clearly on standard Ouchterlony gel diffusion tests for antigen-antibody reactions with specific single reaction lines produced with TARGET which show a line of identity with the line of reaction to ANTI-ASTROCYTIN or ANTI-MALIGNIN antisera (i.e. that produced to the injection of ASTROCYTIN or MALGNIN themselves). Some rabbits, it has been noted, have levels of ANTI-TARGET in their blood prior to being injected with TARGET. These ANTI-TARGET substances, when reacted specifically with TARGET reagent as to be described in tests of human sera, lead to the production of approximately equivalent amounts of the two types of TAG, S-TAG and F-TAG (see later EXAMPLES).

EXAMPLE 8

Detection of Malignant Tumors by Quantitative Production in vitro of TARGET-ATTACHING-GLOBULINS (TAG) from Biological Fluids.

TARGET reagent prepared in accordance with EXAMPLE 6 is washed to remove any unbound RECOGNIN which may be present due to deterioration. The following procedure is satisfactory. TARGET reagent is stirred for two hours at 37° C. with acetic acid, centrifuged, the supernatant decanted, and the optical density of the supernatant read at 266 mµ. If there is any absorbance, this wash is repeated until no further material is solubilized. The TARGET is then resuspended in phosphate buffered saline, pH 7.2. (Standard S-TAG and F-TAG purified from previous reactions of human serum by the procedure described below can be used if available, as reference standards to test the TARGET reagent, as can whole rabbit serum which has been determined to contain S-TAG and F-TAG by other TARGET preparations).

The Slow-Binding (S-TAG) determination is performed as follows: Frozen serum stored more than a few days should not be used. Serum is carefully prepared from freshly obtained whole blood or other body fluid by standard procedures in the art. The following procedure has been found to be satisfactory. Blood is allowed to clot by standing for 2 hours at room temperature in a glass test tube. The clots are separated from the walls with a glass stirring rod, and the blood allowed to stand at 4° C. for a minimum of 2 hours (or overnight). The clots are separated from the serum by centrifuging at 20,000 rpm at 4° C. for 45 minutes. The serum is decanted into a centrifuge tube and centrifuged again at 2000 rpm at 4° C. for 45 minutes. The serum is decanted and a 1% Solution of Methiolate (1 g. in 95 ml. water and 5 ml. 0.2 M bicarbonate buffer pH 10) is added to the extent of 1% of the volume of serum.

Serum samples, prepared by the above or other procedures, of 0.2 ml. each are added to each of 0.25 ml. aliquots of TARGET suspension reagent containing 100–200 micrograms of RECOGNIN per 0.25 ml. TARGET reagent, in duplicate determination. The suspension is mixed at 4° C. in a manner to avoid pellet formation. For example, a small rubber cap rapid shaken may be used for 1–2 seconds and then, with the tubes slightly slanted, they may be shaken in a Thomas shaker for about 2 hours or more. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml. of 0.15 M Saline, centrifuged and the supernatants discarded.

The protein which remains attached to the TARGET is cleaved therefrom and quantitatively determined. For example, 0.2 ml. of 0.25 M acetic acid is added, the suspension shaken for 1 to 2 seconds with a rubber cap shaker, then in a Thomas shaker for about 2 hours in a 37° C. incubator. The tubes are centrifuged at 2000 rpm at 4° C. for 30 minutes. The supernatant is carefully decanted to avoid transfering particles and the optical density of the supernatant is read at 280 mμ. The value of the optical density is divided by a factor of 1.46 for results in micrograms per ml. serum protein (S-TAG). Duplicate determinations should not vary more than 5%. Any other procedure effective for determining protein content may be used, such as Folin-Lowry determination, but standards must be specified to determine the range of control and tumor values of S-TAG minus F-TAG concentration.

The Fast-Binding (F-TAG) determination is performed as follows: Frozen serum stored more than a few days should not be used. Serum is carefully prepared from freshly obtained whole blood or other body fluid by standard procedures in the art. The procedure given above in this EXAMPLE for serum preparation is satisfactory.

Serum samples, prepared by the above or other procedures are allowed to stand at 4° C. for 10 minutes less than the total time the S-TAG serum determinsations were allowed to be in contact with TARGET reagent above [e.g. 1 hour 50 minutes if a "two hour" S-TAG determination was made]. This procedure equilibrates the temperature histories of S-TAG and F-TAG determinations.

Add 0.2 ml. samples of the temperature equilibrated serum to each of 0.25 ml. aliquots of TARGET suspension reagent containing 100–200 micrograms of RECOGNIN per 0.25 ml. TARGET reagent, in duplicate determination. The suspension is then mixed at 4° C. for approximately 10 minutes in a manner to avoid pellet formation. For example, a small rubber cap rapid shaken may be used for 1–2 seconds and then, with the tubes slightly slanted, they may be shaken in a Thomas shaker for approximately 10 minutes. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml. of 0.15 M Saline, centrifuged and the supernatants discarded.

The protein which remains attached to the TARGET is cleaved therefrom and quantitatively determined. The procedure described above in this EXAMPLE for determining S-TAG concentration is satisfactory. Any other procedure effective for determining protein content may be used, such as Folin-Lowry determination, but standards must be specified to determine the range of control and tumor values of S-TAG minus F-TAG concentration.

The final results are expressed as TAG micrograms per ml. of Serum, and equal S-TAG minus F-TAG. TAG values in non-brain-tumor patients and other controls currently range from zero (or a negative number) to 140 micrograms per ml. of serum. TAG values in brain tumor patients currently range from 141 to 500 micrograms per ml. of serum. In the first "blind" study of 50 blood samples conducted according to the procedures of this EXAMPLE utilizing TARGET reagent prepared from Astrocytin and bromoacetylcellulose, 11 of 11 brain tumors and 28 of 32 normals were correctly identified. One of the 4 supposed normals (i.e., non-brain tumor controls) turned out to have a cancer of the thyroid gland which had apparently been successfully treated some years before. The three remaining normals were individuals aged 60–70 who were in poor health, possibly having nondiagnosed cancer. Of the remaining 7 samples, three out of three cases of Hodgkin's Disease were correctly identified; one sample in the tumor range (141–500 μg. TAG/ml.) corresponded to a patient having a severe gliosis, and three samples in the non-tumor range (0–140 μg. TAG/ml.) corresponded to patients having respectively, an intracranial mass diagnosis uncertain but non-tumor, and osteosarcoma (non-brain tumor) and a melanotic sarcoma (non-brain tumor).

A subsequent study conducting according to the procedures of this example utilizing TARGET reagent prepared from MALIGNIN and bromacetylcellulose correctly identified three out of three malignant brain tumors and all normals.

EXAMPLE 9

Diagnosis of Tumor Cells by Immunofluorescence

The compounds Anti-Astrocytin, Anti-Malignin, and S-TAG have been shown to attach preferentially to tumor cells. This specificity permits use of these compounds to diagnose tumor cells in histology sections by conjugating dyes or radioactive substances to Anti-Astrocytin, Anti-Malignin, or S-TAG. Standard labeling techniques may then be used. A procedure using S-TAG is as follows.

One procedure which has been found satisfactory is a modified St. Marie procedure. Human brain tumor specimens are frozen and 5 micron thick sections cut. These are stored in a moist container at minus 70° C. for 4 to 8 weeks before staining. The conjugate may be a standard antiserum such as goat anti-rabbit conjugate. The conjugate is labeled by techniques known in the art with fluoresein or other labeling substance. Fluorescein labeled goat anti-rabbit conjugate as commercially available may be used. The fluorescent technique used was a standard one in which a 1:200 to 1:400 solution of TAG is incubated for about 30 minutes or more on the tumor section, followed by washes to remove unattached TAG. Three washes with phosphate buffered saline has been found satisfactory. Conjugate incubation with fluorescein-labeled conjugate followed by washes is then performed, followed by microscopic inspection. Normal cells and their processes fail to stain both in tumor sections and in control sections of normal non-tumor brain. Fluorescence is brightly present in tumor glial cells and their processes.

EXAMPLE 10

Demonstration that Anti-Astrocytin, Anti-Malignin and S-TAG are Cytotoxic to Tumor Cells Growing in Tissue Culture.

Standard tests for determining cytotoxicity may be used. Generally, the number of cells in a fixed counting chamber, usually arranged to contain about 100 live cells, is counted. These cells are then treated with the agent being tested and the number of cells which are still alive is counted.

In a standard test of cytotoxicity of S-TAG Solution obtained in accordance with the methods of EXAMPLE 8 against cells in tissue culture derived from a patient with a gliblastoma Grade III–IV, well characterized as of glial origin, S-TAG produced death of all cells in the counting chamber even when in high dilution of 1:100 and 1:1000, representing as little as 0.2 and 0.02 µg. of S-TAG per ml. of solution. Similar results are obtained with high dilutions of Anti-Astrocytin and Anti-Malignin.

Both the specifically exhibited in EXAMPLE 9 and the cytotoxicity demonstrated in EXAMPLE 10 are highly relevant to the therapeutic possibilities of Anti-Astrocytin, Anti-Malignin and S-TAG for brain tumors in man. While these therapeutic uses are in the future, the practical diagnostic potential of both of these phenomena for tumor tissue removed at operation but requiring diagnosis by histology is already demonstrated herein.

EXAMPLE 11

Hydrolytic Cleavage of RECOGNINS

A solution of RECOGNIN, in this case either Astrocytin or Malignin at pH between 1 and 2 is allowed to stand in the cold. After 7 to 14 days, TLG chromatography shows the product to have been reduced in molecular weight by approximately 200. When the solution is allowed to stand longer, further units of approximately 200 molecular weight are cleaved every 7 to 10 days. Thus with Astrocytin the molecular weight is reduced from 8,000, and with MALIGNIN the molecular weight is reduced from 10,000, in each case by units of approximately 200 sequentially.

The physicochemical specificities of Astrocytin are retained by each product down to approximately 4,000 molecular weight. The physicochemical specificities of Malignin are retained by each product down to approximately 5,000 molecular weight. This is shown by Ouchterlony gel diffusion tests against Anti-Astrocytin and Anti-Malignin, respectively.

This cleavage can be accomplished enzymatically, as with trypsin and other proteinases, with similar resuts.

The molecula weights of these compounds prepared by hydrolytic cleavage of RECOGNINS may be approximately defined by the following formulae:

For products having the physicochemical specificities of Astrocytin; $4000 + 200\, x = Y$ For products having the physicochemical specificities of Malignin; $5000 + 200\, x = Y$ wherein Y is the molecular weight of the product and X is an integer from 0 to 19.

EXAMPLE 12

Production of Artificial Tissue or Organ with RECOGNINS

A rigid walled tube of plastic, metal, or other suitable rigid material is dipped in or impregnated with a highly concentrated, [i.e., 10 mg./ml.] viscous solution of RECOGNIN, in this case either Astrocytin or Malignin, until all surfaces are fully coated with the RECOGNIN. Alternately, RECOGNIN solution is passed through and around the tube under pressure until all surfaces are fully coated. The tube is then dried in air or in vacuo, or lyophilized. The process of coating is repeated several times in order to build up multiple molecular layers of RECOGNIN coating.

The tube is now ready to be placed in a cavity or in a tissue which contains Astrocytin or Malignin-like precursors in the neighboring tissue or fluid of a living mammal. This artificial tissue or organ may be used to minimize or eliminate reaction which foreign substances without RECOGNIN coating would incite.

Artificial tissues or organs of other geometries may similarly be produced.

What is claimed is:

1. A product, Malignin, derived from brain tumor cells, which forms a single line precipitate with its specific antibody in quantitative precipitin tests and in Ouchterlony gel diffusion tests, is soluble in water and aqueous solutions having an acid or neutral pH, and insoluble at an alkaline pH, and has a spectrophotometric absorption peak wave length of 280 mµ, a molecular weight of about 10,000 and an amino acid composition approximately as follows:

|  | Approx. No. of Residues |
| --- | --- |
| Aspartic Acid | 9 |
| Threonine | 5 |
| Serine | 5 |
| Glutamic Acid | 13 |
| Proline | 4 |
| Glycine | 6 |

-continued

|  | Approx. No. of Residues |
|---|---|
| Alanine | 7 |
| Valine | 6 |
| ½ Cystine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approximate Total | 89 | the amino acids cysteic, hydroxyproline, norleucine, ammonia, isodesmosine, hydroxylysine, lysinonorleucine and gamma-aminobutyric acid being absent in detectable amounts.

2. The antibody, Anti-Malignin, prepared in a mammal in response to the product, Malignin, of claim 1.

3. The product of claim 1 complexed with an inert carrier.

4. The product of claim 3 wherein the inert carrier is bromoacetylcellulose.

5. The product of claim 3 further complexed with the antibody to said Malignin.

6. The product of claim 4 further complexed with the antibody to said Malignin.

7. Polypeptides having the physicochemical specificities of the product of claim 1 and derived therefrom by sequential cleavage of units of approximately a molecular weight of 200 down to a molecular weight of approximately 5000.

8. Polypeptides having the physicochemical specificities of the product of claim 1, and derived therefrom, having a molecular weight approximately defined by the formula $5000+200X=Y$; wherein Y is the molecular weight of the polypeptides; and X is an integer from 0-19.

9. A process for producing a product, Malignin, which comprises extracting artificial brain tumor cells grown in culture with a neutral buffer by repeated disruption of the tissue to solubilize protein fractions, separating from the resulting extract the fraction having a pK range of about 1 to 4, and isolating the product having a molecular weight of about 10,000, said product, Malignin, derived from brain tumor cells, which forms a single line precipitate with its specific antibody in quantitative precipitin tests and Ouchterlony gel diffusion tests, is soluble in water and aqueous solutions having an acid of neutral pH, and insoluble at an alkaline pH, and has a spectrophotometric absorption peak wave length of 280 mμ, a molecular weight of about 10,000 and an amino acid composition approximately as follows:

|  | Approx. No. of Residues |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cystine | 1 |
| Methionine | 2 |
| Isoleucine | 4 |
| Leucine | 8 |
| Tryosine | 3 |
| Phenylalanine | 3 |
| Lysine | 6 |
| Histidine | 2 |
| Arginine | 5 |
| Approximate Total | 89 | the amino acids cysteic, hydroxyproline, norleucine, ammonia, isodesmosine, hydroxylysine, lysinonorleucine and gammaaminobutyric acid being absent in detectable amounts.

10. The process of claim 9 wherein said step of separating the fraction having a pK range of from about 1 to 4 is carried out by adding said extract of solubilized proteins into a chromatographic column and eluting with increasingly acidic solvents.

11. The process of claim 10 wherein said isolating is carried out by filtering the eluate to obtain a fraction containing Malignin and separating Malignin therefrom by thin layer gel chromatography.

* * * * *